United States Patent
Fleury

(10) Patent No.: US 7,257,989 B2
(45) Date of Patent: Aug. 21, 2007

(54) METHOD AND DEVICE FOR MEASURING PHYSICAL CHARACTERISTICS OF A SOLID POROUS SAMPLE

(75) Inventor: Marc Fleury, La Celle Saint Cloud (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 184 days.

(21) Appl. No.: 11/014,781

(22) Filed: Dec. 20, 2004

(65) Prior Publication Data

US 2005/0240360 A1    Oct. 27, 2005

(30) Foreign Application Priority Data

Dec. 19, 2003  (FR) .................................. 03 15199

(51) Int. Cl.
   *G01N 15/08* (2006.01)
(52) U.S. Cl. ......................................................... 73/38
(58) Field of Classification Search .................. 73/38
   See application file for complete search history.

(56) References Cited

U.S. PATENT DOCUMENTS

| | | | |
|---|---|---|---|
| 4,893,504 A | 1/1990 | O'Meara, Jr. et al. | |
| 5,463,894 A * | 11/1995 | Fleury et al. | 73/38 |
| 6,185,985 B1 * | 2/2001 | Fleury et al. | 73/38 |
| 6,490,531 B1 | 12/2002 | Goglin et al. | |

FOREIGN PATENT DOCUMENTS

| | | | | |
|---|---|---|---|---|
| EP | 0 586 001 A1 | 3/1994 | | |
| GB | 2325526 A | * 11/1998 | ..................... | 73/38 |

OTHER PUBLICATIONS

Raghuraman, B. et al., "Capillary Pressure and Resistivity Measurements Using the Centrifuge: A New Interpretation Method," SCA-9811, The Society of Core Analysts, 1998.*

(Continued)

*Primary Examiner*—Daniel S. Larkin
(74) *Attorney, Agent, or Firm*—Antonelli, Terry, Stout & Kraus, LLP.

(57) ABSTRACT

A method measures the physical characteristics of at least one solid porous sample (S) saturated with a first fluid by carrying out drainage or imbibition phases, in the presence of a second fluid with a different density from that of the first fluid. A sample saturated with a first fluid, such as brine, is placed in a vessel filled with a second fluid. By means of a centrifugation assembly, the sample is drained until a final saturation pressure is established in the sample. In a second phase, the sample can be soaked. The drainage or imbibition phases are carried out by interposing a porous plate (1) between the sample (S) and the vessel in which it is placed, the porous plate being wettable by the first fluid or the second fluid with preferably an inlet pressure greater than the highest capillary pressure imposed on the face of the sample in contact with the porous plate and perforated with perforations whose number and cross section are adjusted to enable rapid drainage of the fluid contained in the core sample and obtain a substantially uniform saturation profile. The method is applicable in particular to petrophysical measurements.

9 Claims, 4 Drawing Sheets

OTHER PUBLICATIONS

Fleury, M. et al., "Capacitance Technique for Measuring Production While Centrifuging," SCA-9833, Proceedings of the International Symposium of the Society of Core Analysts, Sep. 14-16, 1998, The Hague., pp. 1-11.*

Lombard, J-M. et al., "Measurement of Capillary Pressure Curves at Reservoir Conditions," SCA2002-09, The Society of Core Analysts, 2002, pp. 1-16.*

Fleury, M. et al., "Combined Resistivity and Capillary Pressure Measurements Using Micropore Membrane Technique," Journal of Petroleum Science and Engineering, vol. 19, 1998, pp. 73-79.*

Longeron, D. et al., "Water-Oil Capillary Pressure and Wettability Measurements Using Micropore Membrane Technique," SPE 30006, Society of Petroleum Engineers, Nov. 14-17, 1995, pp. 543-553.*

* cited by examiner

METHOD AND DEVICE FOR MEASURING PHYSICAL CHARACTERISTICS OF A SOLID POROUS SAMPLE

The present invention relates to a method and a centrifugation device for measuring physical characteristics of a solid porous sample.

PRIOR ART

In programs of special analysis of rock samples or core samples taken from a medium, such as an underground region, establishment of initial representative water saturation plays a key role in core sample preparation. The point is to establish fluids in proportions representative of those originally present in the reservoir region after migration of the oil. Typically, if the effectiveness of water injection is to be studied and the capillary pressure curve and relative permeability curve are to be measured, the initial saturation Swi is important and must be representative of the in-situ conditions. The term "initial" is used advisedly here to avoid any confusion with the term "irreducible" which describes the asymptotic saturation obtained with a high capillary pressure for a given set of fluids. In a transition zone, these two saturations are very different.

According to a standard procedure, the samples are extracted from full-diameter core samples, then cleaned with appropriate solvents. The samples are then brought to initial saturation (Swi) or irreducible saturation (Swirr) depending on their position in terms of capillary pressure, and aged with crude oil. At this stage, the amount of water present also plays a decisive role in obtaining a representative state of wettability. This is why a substantial effort is generally made to establish this initial saturation (Swi).

Several known techniques enable this condition to be reached. For example, the water-saturated sample can be confined in a cell and this water can be displaced by injecting oil. It is known, however, that it is difficult to obtain low water saturations, essentially because of the presence of heterogeneities despite the use of a viscous oil (typically 50 cP). A viscous oil can also be somewhat impractical for low permeabilities. The average saturation can hence still be high after breakthrough and residual production can be significant and take several days. Moreover, the saturation profile is highly nonuniform, as is the case with standard centrifugation. This profile can however be reduced by reversing the injection direction. Although centrifugation is the most effective technique for saturating core samples, it cannot be used to establish saturation (Swi) because of the presence of a high saturation profile which can give rise to interpretation problems in later injection experiments. For example, one may cite the substitution technique, the drainage method for which the main difficulty is controlling or imposing the salinity and the saturation profile. The ideal would be to use a capillarity displacement process, as is the case in situ, with an experimental time compatible with the schedule of the development or evaluation program, which is generally short. To avoid non-uniform profiles and obtain low water saturation, the porous plate method can be used instead of the above-mentioned techniques. The experiments are time-consuming, taking a few weeks to a few months, particularly in the case of long core samples. Moreover, the capillary contact between the core sample and the porous plate is often difficult to optimize and may lead to a low success rate.

Finally, the centrifugation technique is probably the most attractive solution. This is a displacement process dominated by capillarity, which is rapid and inexpensive and has a number of practical advantages. Its main drawback is however the non-uniformity of the saturation profile and, for certain centrifuges, the limit imposed by the length of the core samples.

METHOD AND DEVICE ACCORDING TO THE INVENTION

The method according to the invention enables physical characteristics of a solid porous sample saturated with a first fluid to be measured by carrying out drainage and imbibition phases in the presence of a second fluid with a different density from that of the first fluid. It involves the use of a centrifugation assembly comprising at least one vessel for the sample, adjusted to apply a centrifugal force to the sample, said force being oriented in the elongation direction so as to displace the first fluid by the second fluid and determine the final value of the displaced-fluid saturation.

The drainage or imbibition phases are conducted by applying a porous plate against one end face of the sample traversed by the displaced fluid, said porous plate being wettable by the displaced fluid and being perforated with perforations whose number and cross section are adjusted to enable rapid drainage of the fluid contained in the core sample and obtain a substantially uniform saturation profile.

If the displaced phase is the heavier phase (water for example in a drainage phase), a porous plate is interposed between the sample and its support in the vessel. If the displaced phase is the lighter phase (such as oil in an imbibition phase), this porous plate is placed against the sample, on the side closest to the rotational axis of the centrifugation assembly.

The perforated porous plate is made so that preferably the inlet pressure is higher than the highest capillary pressure imposed at the face of the sample in contact with the porous plate.

According to one embodiment, a drainage phase of a sample saturated with a first liquid (L1) is carried out by placing the sample in contact with a perforated porous plate wettable by the first fluid disposed on the side of the sample furthest from the rotational axis of the centrifugation assembly.

The porous plate is made for example from a material, such as a porous ceramic, normally used in capillary pressure experiments, or any other material whose properties are equivalent such as, in particular, a porous cement.

According to another embodiment, a phase of sample imbibition is carried out by placing the sample in contact with a perforated porous plate wettable by the second fluid disposed on the side of the sample closest to the rotational axis of the centrifugation assembly.

In the context of this embodiment, a perforated porous plate made for example from a porous, permeable material, such as TEFLON®, is used.

The device according to the invention enables measurement of the physical characteristics of at least one solid porous sample saturated with a first fluid by carrying out drainage or imbibition phases, in the presence of a second fluid with a different density from that of the first fluid. It has a centrifugation assembly including at least one elongate vessel provided with a chamber for a sample, each vessel being attached at the end of an arm integral with a rotational axis, drive means for driving the arm rotationally and creating a centrifugal force oriented in the elongation direction of the vessel, and means for determining the final saturation value of the displaced fluid.

The device also has a porous plate in contact with the sample, said plate being perforated with perforations whose number and cross section are adjusted to enable rapid drainage of the fluid contained in the core sample and obtain a substantially uniform saturation profile.

Preferably, the porous plate is made so that there is a higher inlet pressure than the highest capillary pressure imposed at the face of the sample in contact with the porous plate.

The method and device presented here are highly effective in establishing an irreducible saturation at a capillary pressure representative of the field considered. The residual oil saturation (Sor) will thus also be representative because it depends on (Swi) and, something which is equally important, the wettability will be representative because it depends on the amount of water present in the porous system.

PRESENTATION OF FIGURES

The characteristics and advantages of the method and device according to the invention will appear more clearly from reading the description hereinbelow of a non-limiting exemplary embodiment, with reference to the attached drawings.

Figure 2A:
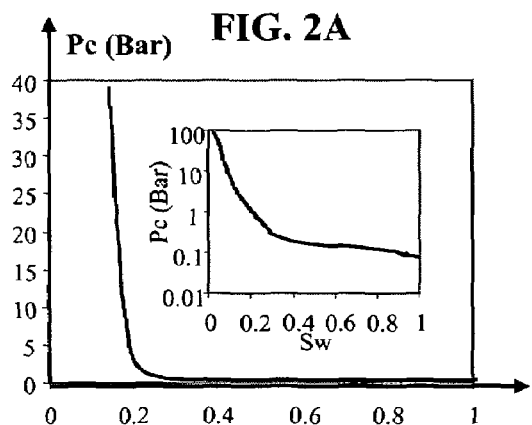
FIG. 2A shows examples of varying the capillary pressure Pc as a function of water saturation Sw.
Figure 2B:
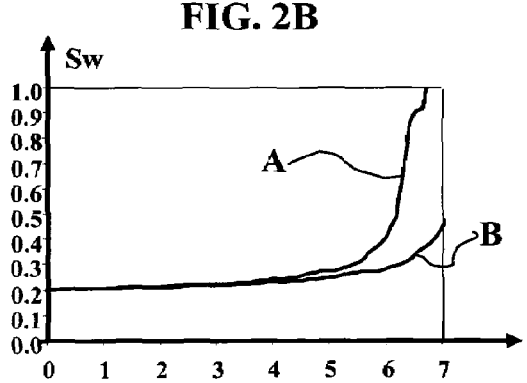
Figure 2C:
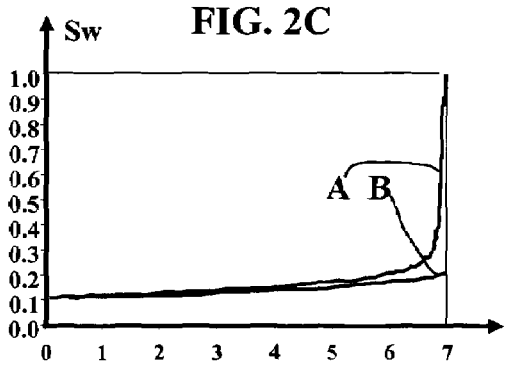
Figure 2D:
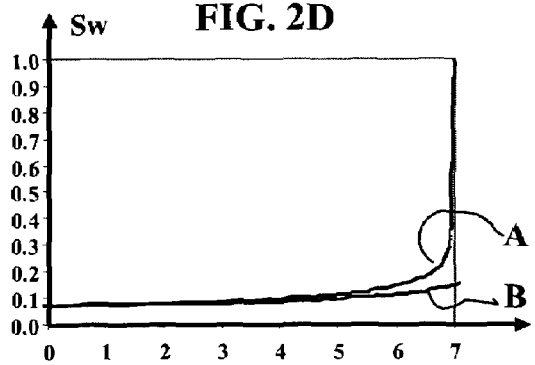
Figure 3:
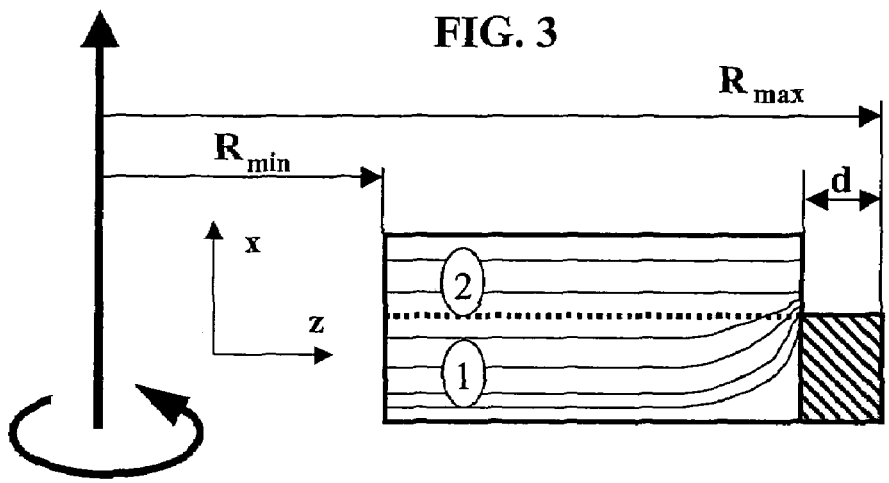
Figure 4B:
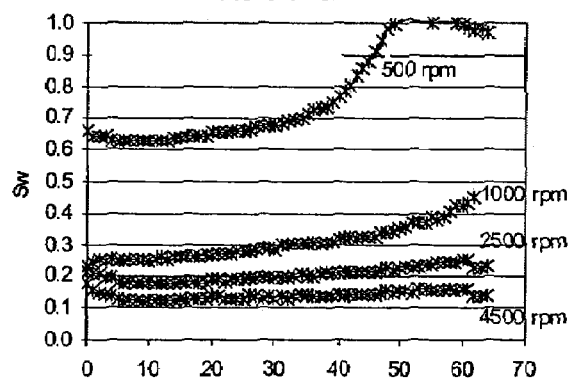
Figure 4A:
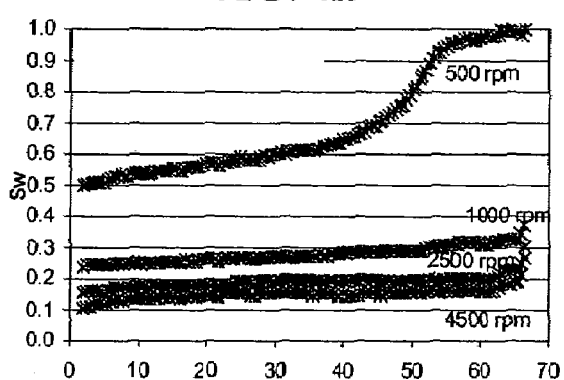
Figure 4D:
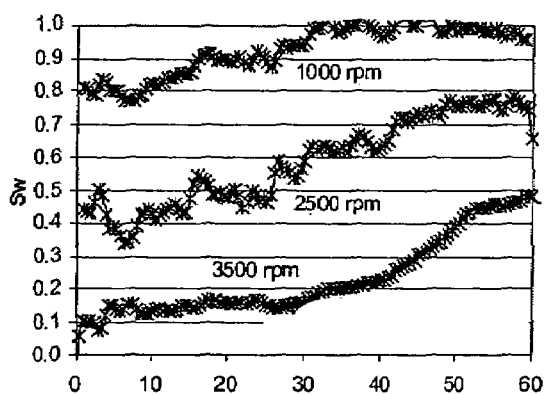
Figure 4C:
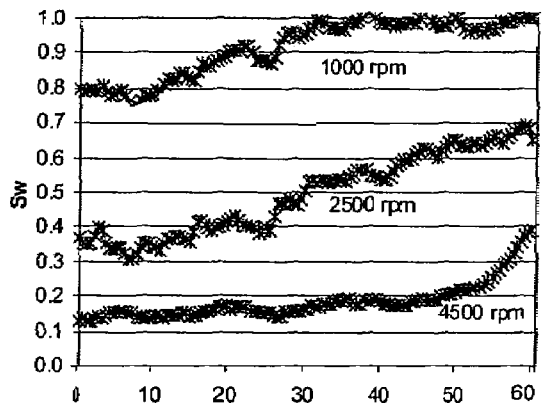
Figure 5:
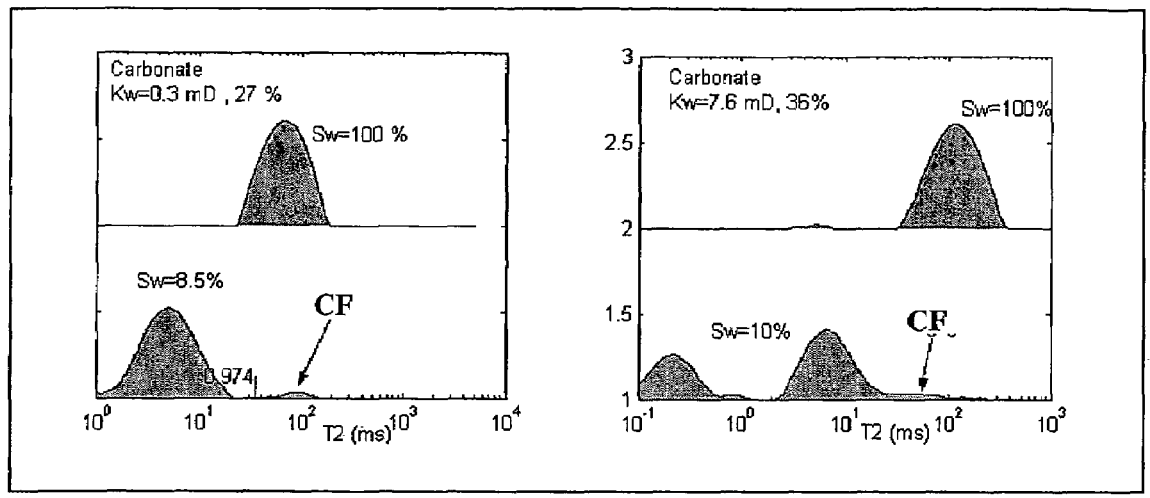
Figure 6:
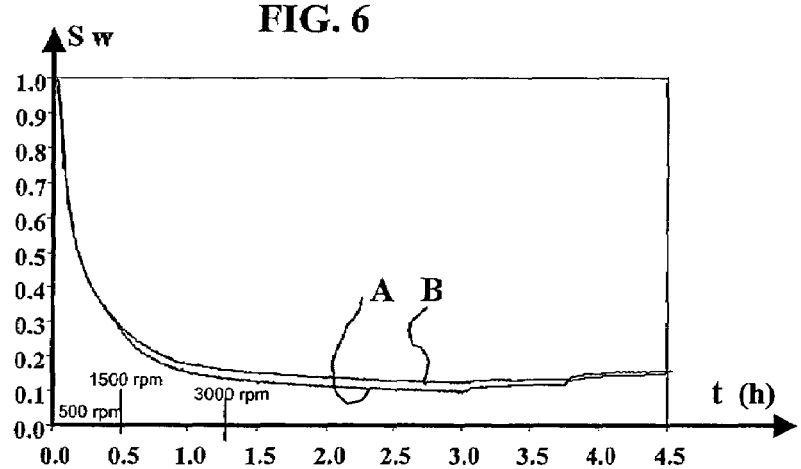
Figure 7:
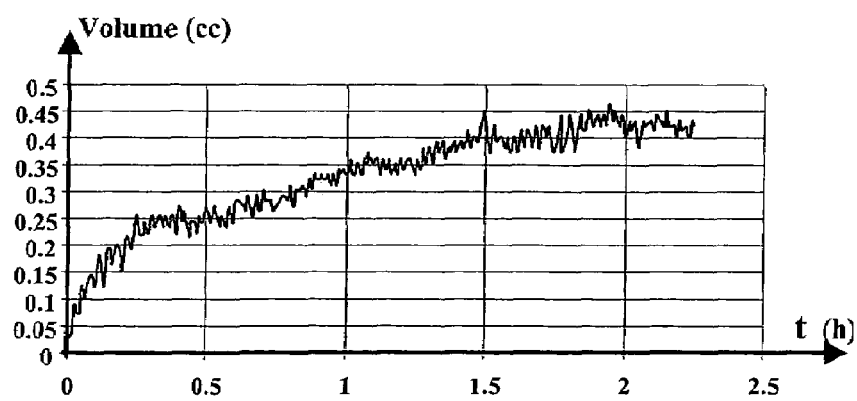
Figure 8:
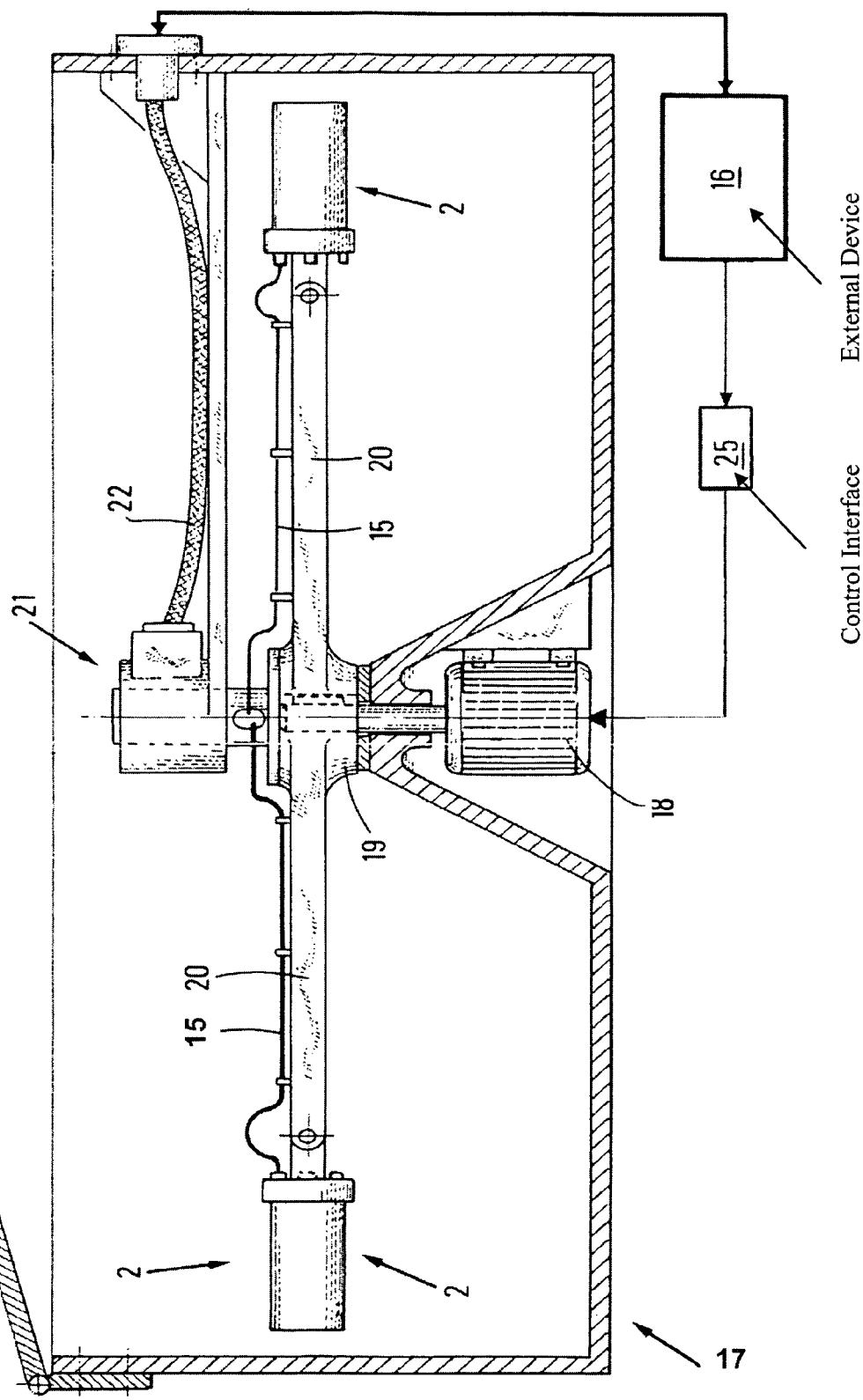

FIGS. 2B, 2C, and 2D show, for different speed stages, examples of a saturation profile calculated without the porous plate (A) and with the porous plate (B) (air-water system) along the length of a core sample;

FIG. 3 shows the flow lines of the fluid depending on whether they correspond to a zone 2 facing a perforation or a zone 1 facing a non-perforated part, said zones having different capillary pressures;

FIGS. 4A to 4D show different examples of variations, obtained by x-ray CT scanning, of the saturation Sw along a sandstone core sample with a porous plate (FIG. 4A) and without a porous plate (FIG. 4B) and of a carbonate core sample (FIGS. 4C, 4D) with a porous plate (FIG. 4C) and without a porous plate (FIG. 4D) for different rotational speeds; the final saturation profile is uniform for sandstone and compact for carbonate;

FIG. 5 shows a capillary footprint (CF) detected by measuring relaxation times by NMR; the existence of a hump for the relaxation time of the 100% saturated core sample indicates a non-uniform profile;

FIG. 6 shows, by comparison, two curves of Sw variation as a function of time obtained with the porous plate (A) and without the porous plate (B) for two small core samples (air/water);

FIG. 7 shows the production observed when the oil-water level is displaced rapidly starting from the outlet face (Rmax-d, FIG. 1) of a sandstone core sample (K=610 mD, $\phi$=23%, L=5.9 cm) and proceeding to the outlet face of the porous plate (Rmax) subjected to centrifugation; and FIG. 8 shows an example of a centrifugation assembly for implementing the method.

DETAILED DESCRIPTION OF THE INVENTION

Principle

The method is implemented using a centrifugation device as described for example in French Patent 2,699,282 (U.S. Pat. No. 5,463,894), French Patent 2,763,690, or French Patent 2,772,477 (U.S. Pat. No. 6,185,985) by the applicant, shown detail in FIG. 8.

A centrifugation device suitable for implementing the method has for example (FIG. 8) a tank 17 and an electric motor 18 whose shaft drives a hub 19 rotationally. Two (or four) identical arms 20 are mounted oppositely two by two on hub 19. Containers or vessels 2 are pivotably mounted at the ends of each of arms 20 so as to line up spontaneously with the direction of the centrifugal force applied, and become rotationally balanced with each other. The sample to be evaluated is placed in at least one of vessels 2. Means (not shown) located in each vessel enable the gradual movements of the interface between the two liquids during the drainage and reimbibition operations to be measured.

Cables 15 associated with the various measuring means are connected to a multi-line rotating electrical connector 21 of a known type mounted on hub 19. The stator of this rotating connector 21 is connected by a cable 22 to an external device 16 designed to control the variation in rotational-speed steps of the motor by means of a control interface 25, and to process the signals coming from the measuring means in the vessels 2.

The sample S saturated with a liquid L1 (brine for example) is placed in a vessel containing another fluid L2 with a different density (such as oil). When the rotating arm is made to rotate, a centrifugal force is applied in order to study the displacements of fluids in the sample during at least two distinct phases. In a first drainage phase, the assembly is subjected to a centrifugal force directed along the length of the container in order to exert an expulsion force thereon, which tends to cause part of first fluid L1 to flow out. At the same time, some of fluid L2 flows into the sample. The two fluids move inside the sample until a position of equilibrium is reached, where the force due to the capillary pressure in the pores compensates for the centrifugal force exerted.

The average saturation of the sample can be determined from the precise measurement of the amount of initial fluid extracted at the end of centrifugation, and this saturation will be practically uniform along the sample.

For specific implementation of the method, the sample or core sample with length L is placed in vessel 2 with its base resting (at a distance Rmax-d from the axis of rotation of the rotating arm) on a perforated porous plate 1 with thickness d (FIG. 1) wettable by first fluid L1. This porous plate can be made for example of porous ceramic, porous cement, etc. Its inlet pressure is high enough to prevent fluid L2 or air from penetrating inside. Its opposite end is at the distance Rmin from this same axis. The porous plate enables a near-uniform saturation profile to be obtained (elimination of capillary footprint) and the perforations preserve as high as possible a flowrate during centrifugation.

Leaving 2D effects out of count, the capillary pressure at a radius r is given by:

$$P_c(r) = \frac{1}{2}\omega^2 \Delta\rho (R_{max}^2 - r^2) \quad (1)$$

where $\Delta\rho$ is the difference in density between water and air or oil and $\omega$ is the rotational speed of the centrifuge. Assuming capillary contact between the core sample and the porous plate, equation 1 indicates simply that the capillary pressure at the outlet face (Rmax−d) of the core sample is different from zero. Thus, the outlet face of the core sample will be desaturated as a function of the capillary pressure curve.

From equation 1, we can express the capillary pressure ratio at the inlet $Pc(Rmin)$ and at the outlet $Pc(Rmax-d)$ of the core sample:

$$\frac{PcInlet}{PcOutlet} = \frac{R_{max}^2 - R_{min}^2}{R_{max}^2 - (R_{max} - d)^2} \quad (2)$$

Typically, the porous plate has a thickness of 1 cm and the ratio referred to above is 6.1 and 8.7 for L=6 and 10 cm respectively (Rmax=25 cm). For a given capillary pressure curve, this ratio indirectly expresses the minimum and maximum saturation in the sample.

To illustrate the effect of the porous plate, we calculated the saturation profiles at different rotational speeds (FIGS. 2B, 2C, and 2D) with this plate (B) and without this plate (A), for a measured capillary pressure (FIG. 2A, sW=f(Pc) and Pc=f(r) from equation 1). When the rotational speed is sufficient, the saturation profile is nearly constant because all of the core sample is at a pressure corresponding to the asymptotic part of the Pc curve.

In the saturation profile example calculated with and without the porous plate (air-water system) shown in FIGS. 2B, 2C, and 2D, the capillary pressure was deduced by injecting mercury. Because of the porous plate, the profile Sw is nearly uniform at constant speed (>2500 rpm;). The inlet face is located at a radius Rmin=17 cm (x=0 along the core sample).

Effect of Perforations, Boundary Conditions

In the first place, the porous plate is made to have an inlet pressure greater than the highest capillary pressure at radius r=Rmax-d. This is why it is never desaturated. Desaturation of the porous plate would bring about a considerable reduction in flow (relative permeability effect) and uncertainties regarding the mass balance for calculating saturation, and would not facilitate good capillary contact. In the present case, the air-water inlet pressure of the porous plate is about 3.5 bars (0.35 Mpa). The drawback is its low permeability ($K_c$ is about 0.2 mD for example). Hence, if it were not perforated, the flow would be dominated by the porous plate as shown by the relationship $$\frac{L+t}{K_T} = \frac{L}{K_S} + \frac{t}{K_c} \quad (3)$$

For example, for a core sample with permeability $K_s$=100 mD, the total permeability $K_T$ would be 1.2 mD, representing a considerable loss.

The perforations enable the kinetics of the system to be dominated by the core sample and not by the porous plate, as shown by the tests. However, the question of boundary conditions arises, and is not easy to resolve. To demonstrate that the perforations do not modify the capillary pressure at the outlet face, we will consider the system shown in FIG. 3. Above a perforation (zone 2) and above the porous plate (zone 1), the capillary pressures are vertically in equilibrium according to:

$$P_{c1}(r) = \frac{1}{2}\omega^2 \Delta\rho(R_{max}^2 - r^2) \, et \, P_{c2}(r) = \frac{1}{2}\omega^2 \Delta\rho((R_{max} - t)^2 - r^2) + C \quad (4)$$

where C is an unknown integration constant. At a given rotation radius r4, a difference in capillary pressure in zones 1 and 2 would bring about a flow that cannot be balanced by any force in direction x. This is why, in order to obtain equilibrium in direction x, the capillary pressures Pc1 and Pc2 must be equal and likewise the saturations in zones 1 and 2 must be equal. Desaturation also occurs, particularly at the outlet face of the core sample which has no porous plate (zone 2). In practice, the perforations must not be too large (size of zone 2 too large relative to 1). For reasons linked to mechanical constraints, the diameter of the perforations is 2 mm and the number of perforations is empirically set at twenty (the average distance between the perforations would thus be about 0.8 cm). Most of the fluid expelled from the core sample will pass through these perforations. The choice of the number of perforations, their diameter, and their arrangement must meet certain requirements: maximizing the contact surface area between the samples and the porous plate to ensure that the plate has good mechanical strength, while enabling the fluids to be properly evacuated.

Practical Aspects

In practice, the SPP technique has several advantages:

manipulation is simple and many core samples can be desaturated simultaneously (six in the present case); by using large-diameter centrifuges (Rmax=25 cm) and using an intermediate speed ($\omega_{max}$=4900 rpm), it is possible to use core samples whose lengths can reach 12 cm and a high capillary pressure can be obtained (64 bars air-water, 31 bars dodecane-water);

capillary contact is easy to achieve (if both faces of the core samples are plane) because the centrifugal forces push the core sample against the porous plate.

The main difficulty is avoiding damage to the core samples, especially when they are long. In certain cases, it may be impossible to obtain a uniform saturation profile when the rotational speed must be limited. There are two solutions to this problem: (i) using a longer porous plate to reduce the ratio between inlet Pc and outlet Pc (equation 2) and minimizing the rotational speed and/or (ii) turning the core sample around and rotating at the same speed for a similar period of time.

The method can be applied to air/water drainage or to oil/water drainage. Air/water drainage has certain advantages however relative to oil/water drainage. First, as the difference in density is greater, a lower speed is required, which presents a smaller risk of potential damage to the core sample. Next, the desaturated air/water core sample is easier to install in an injection cell for later experiments. The air can be replaced by oil by using a displacement sequence miscible with C1, cyclohexane, and crude oil. In the third place, finally, calculation of saturation is more precise.

According to a standard procedure, three measurements are made to estimate the final average saturation: measurement of the volume expelled from the core sample, measurement of the weight of the core sample (for a granulometric loss estimate), and NMR measurement (before and after centrifugation).

Validation of Method

A number of experiments were conducted to show the validity of the method proposed. First, we checked the effect of the porous plate on saturation profiles. Next, we studied the kinetics of the desaturation process with and without the porous plate.

Saturation Profiles by CT Scanning

Saturation profiles were measured on two core samples, one sandstone and the other carbonate, with and without a porous plate in the form of an end support (two experiments were done sequentially, the core samples being 100% resaturated between them). The effect of the porous plate appears clearly at low speeds and intermediate speeds (FIGS. 4A and 4B) for sandstone. At high speeds, the experiment done without the porous plate may appear to give a uniform profile, but this is due to lack of X Scanner measurement resolution. With the porous plate, we are sure of achieving a truly uniform profile. For compact carbonate, also shown in FIGS. 4C and 4D, the profiles obtained at low speeds are similar because the rotation time is too short. At the maximum speed, the difference is obvious. However, the profile obtained in the presence of the porous plate is not entirely uniform. In this case, the core sample must be turned around, and centrifugation continued. For both core samples, the typical rotation time was between twenty-four and forty-eight hours.

Another method for checking the uniformity of the saturation profile consists of making relaxation measurements by NMR before and after centrifugation (FIG. 5). This rapid measurement method is also very precise for estimating the final saturation of air/water systems. When saturation is uniform, the $T_2$ distribution at (Swirr) should not present a peak at the relaxation time of the 100%-saturated core sample because the relaxation times $T_2$ are displaced to lower values in proportion to saturation (from the fundamental relationship $T_2 \infty V/S$; as shown by the distribution, the principal peaks are modified by a factor of ten when saturation drops to 10%). This is observed for the low-permeability carbonate shown in FIG. 5 (left box). For the highest-permeability core sample (right box), $T_2$ at high saturation does not extend to the region of the fully saturated core sample, indicating a negligible capillary footprint.

Kinetics with and without Perforated Porous Plate

We tested the kinetics of the desaturation process with and without a porous plate. As explained above, the perforations should not substantially affect the flowrate. This appears clearly when we compare the transient saturation upon centrifugation of two small core samples with average permeability (about 180 mD; note that one of these core samples is shorter than the other so that there is a similar pressure loss). Low saturation is achieved after a few hours in both cases.

In the example of FIG. 6 showing a comparison of transient production with and without the porous plate for two small air/water centrifugations, the rotational speed was initially set at 500 rpm (t=0) then at 1500 rpm (t=0.5 h), and at 3000 rpm (t=1.25 h). Low saturation was reached in a few hours with displacement dominated by capillarity. For the largest sandstone core sample, L=6 cm, Kw=194 mD; for the smallest core sample, L=5 cm, Kw=171 mD.

Figure 1:
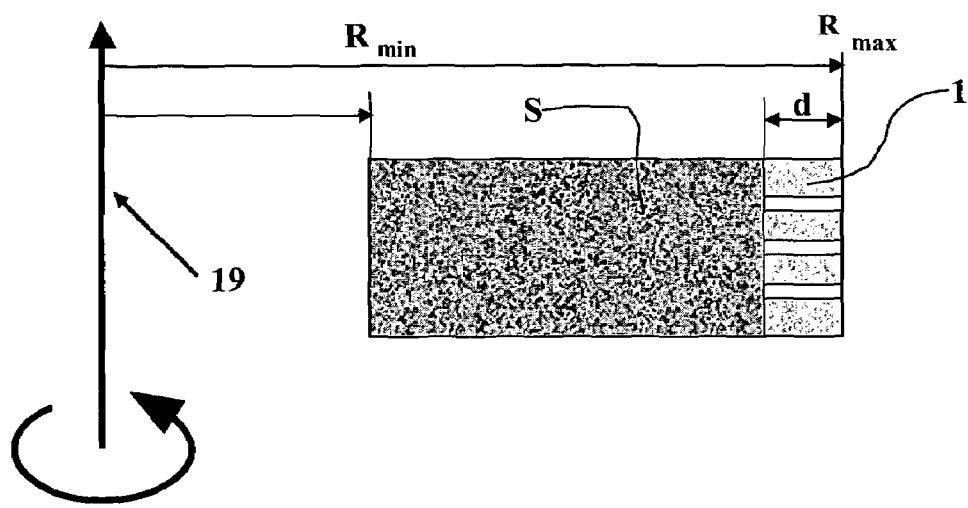
FIG. 1 is a diagram of an apparatus for implementing the method.

It is useful to find out the typical time necessary to drain the capillary footprint alone (FIG. 7). During this experiment, a sandstone core sample was first centrifuged by the PWC technique described in:

Fleury et al., Proceedings of the International Symposium of the Society of Core Analysts, The Hague, Sep. 14-16, 1998 and the oil-water level was kept continuous near the outlet face of the core sample (Rmax-d, FIG. 1). At time 0 (FIG. 7), the level went to Rmax and production was measured. We observed that stable saturation was reached in a few hours and that this time depends essentially on the porous plate, not on the core sample (this observation also applies to air/water drainage). The saturation stabilizes fairly rapidly despite the low permeability of the porous plate because only a small fraction of the core sample has to be drained (approximately a hemisphere with a diameter equal to the distance between the perforations).

In general, the rotation time depends on various parameters (length, capillary pressure, and relative permeability to water at low saturation) and it is difficult to make a precise prediction. Experience shows that, even for a compact formation, the target saturation may be reached in forty-eight hours.

Imbibition

Thus far, an application of the method has been described whereby the sample in contact with the furthest side (Rmax in FIG. 1) of the axis of rotation of the centrifuge with a porous plate wettable by the first fluid L1 has been described.

It is possible to supplement the previous drainage stage by an additional imbibition stage. This time, it is the previously drained side of the sample closest to the center of rotation of the centrifuge (Rmin, FIG. 1) that is placed in contact with a porous plate wettable by the second fluid L2. This may for example be a TEFLON® plate. It is also provided with holes for passage of second fluid L2.

For this second supplementary stage, the same precautions as for the drainage phase must be taken regarding the number, diameter, and position of the holes in the porous plate.

It may be observed, as a conclusion, that the combination of the centrifuge and the porous plate described exploits the advantages of these two techniques while eliminating their main drawbacks. For consolidated core samples with medium/high permeability (>10 mD), we obtained a uniform profile, as low water saturation was reached in a few hours/days. In the case of low to very low permeability, the saturation profile can be almost uniform. In this case, an additional experiment should be made, consisting of turning the sample around and centrifuging it under the same conditions.

What is claimed is:

1. Method for measuring the physical characteristics of a solid porous sample saturated with a first fluid by carrying out drainage or imbibition phases, in the presence of a second fluid with a different density from that of the first fluid, involving the use of a centrifugation assembly having at least one vessel for the sample, adjusted for applying to the sample a centrifugal force that is oriented in the elongation direction and variable so as to displace the first fluid by the second fluid, and determination of a final saturation value for displaced-fluid saturation, wherein the drainage or imbibition phases are carried out by applying a porous plate against one end face of the sample traversed by the displaced fluid, said porous plate being wettable by the displaced fluid and being perforated with perforations of a number and cross section that enable rapid drainage of the fluid contained in the core sample and obtain a substantially uniform saturation profile.

2. Method according to claim 1, wherein the perforated porous plate is made such that there is an inlet pressure higher than the highest capillary pressure imposed at the face of the sample in contact with the porous plate.

3. Method according to claim 1, wherein the drainage phase of the sample saturated with the first liquid is carried out by placing the sample in contact with the perforated porous plate wettable by the first fluid disposed on the side of the sample furthest from the rotational axis of the centrifugation assembly.

4. Method according to claim 3, wherein the porous plate is a porous ceramic or is made of cement.

5. Method according to claim 3, wherein the phase of sample imbibition is carried out by placing the sample in contact with the perforated porous plate wettable by the second fluid disposed on the side of the sample closest to the rotational axis of the centrifugation assembly.

6. Method according to claim 5, wherein the perforated porous plate is made of a porous and permeable material wettable by the second fluid.

7. Method according to claim 5, wherein the perforated porous plate is made of fluorinated ethylene propylene.

8. Device for measuring the physical characteristics of at least one solid porous sample saturated with a first fluid by carrying out drainage or imbibition phases, in the presence of a second fluid with a different density from that of the first fluid, having a centrifugation assembly including at least one elongate vessel provided with a chamber for a sample, each vessel being attached at the end of an arm integral with a rotational axis, drive means for driving the arm rotationally and creating a centrifugal force oriented in the elongation direction of the vessel, means for determining the final saturation value of the displaced fluid, and a porous plate in contact with the sample, said plate being perforated with perforations of a number and cross section that enable rapid drainage of the fluid contained in the core sample and obtain a substantially uniform saturation profile.

9. Device according to claim 8, wherein the porous plate is made such that there is a higher inlet pressure than the highest capillary pressure with the face of the sample in contact with the porous plate.

* * * * *